United States Patent [19]
Hubbs

[11] Patent Number: 5,817,490
[45] Date of Patent: Oct. 6, 1998

[54] ENZYMATIC PROCESS FOR THE MANUFACTURE OF ASCORBIC ACID 2-KETO-L-GULONIC ACID AND ESTERS OF 2-KETO-L-GULONIC ACID

[75] Inventor: John Clark Hubbs, Kingsport, Tenn.

[73] Assignee: Eastman Chemical Company, Kingsport, Tenn.

[21] Appl. No.: 845,295

[22] Filed: Apr. 25, 1997

Related U.S. Application Data

[60] Provisional application No. 60/017,879 May 17, 1996.
[51] Int. Cl.$^6$ .............................. C12P 7/58; C12N 9/14; C12N 1/20; C12N 1/00
[52] U.S. Cl. .................. 435/137; 435/195; 435/197; 435/219; 435/252.3; 435/836; 435/847; 435/913; 435/921; 435/933; 536/23.2
[58] Field of Search .................... 435/137, 195, 435/197, 219, 252.3, 836, 913, 921, 933, 847; 536/23.2

[56] References Cited

U.S. PATENT DOCUMENTS

| | | | |
|---|---|---|---|
| 2,301,811 | 11/1942 | Reichstein | 260/344 |
| 5,008,193 | 4/1991 | Anderson et al. | 435/138 |
| 5,441,882 | 8/1995 | Estell et al. | 435/222 |

FOREIGN PATENT DOCUMENTS

| | | |
|---|---|---|
| 0 207 763 | 1/1987 | European Pat. Off. . |
| 0 292 303 | 11/1988 | European Pat. Off. . |
| 0 401 704 | 12/1990 | European Pat. Off. . |
| 0 514 694 A1 | 4/1992 | European Pat. Off. . |
| 466548 | 6/1937 | United Kingdom . |
| WO 85/01745 | 4/1985 | WIPO . |
| 87/00839 | 2/1987 | WIPO . |

OTHER PUBLICATIONS

D. G. Hayes, "The Catalytic Activity of Lipases Toward Hydroxy Fatty Acids–A Review", *Journal of the American Oil Chemists' Society,* vol. 73, No. 5, pp. 543–549, May 1, 1996.

T. Reichstein et al., *Helv. Chim. Acta,* vol. 17, pp. 311–328 (1934).
T. Sonoyama et al., *Applied and Envtl. Microbiology,* vol. 43, pp. 1064–1069 (1982).
M. Shinjoh et al., *Applied and Envtl. Microbiology,* vol. 61 pp. 413–420 (1995).
S. Anderson et al., *Science,* vol. 230, pp. 144–149 (1985).
Yamazaki, *J. Agri. Chem. Soc. Japan,* vol. 28, pp. 890–894 (1954) (translation not included).
*Chemical Abstracts,* vol. 50, 5992d.
F. Thiel, *Catalysis Today,* pp. 517–536 (1994).
A. L. Gutman et al., *Tetrahedron Lett.,* vol. 28, pp.3861–3864 (1987).
A. L. Gutman et al., *Tetrahedron Lett.,* vol. 28, pp. 5367–5368 (1987).
*Enzyme Nomenclature* (Academic Press, 1992) (cover pages only).
E. L. Smith et al., *J. Biol. Chem.,* vol. 243, pp. 2184–2191 (1968).
M. Matsushima et al., *FEBS Lett.,* vol. 293, pp. 37–41 (1991).
J. Uppenberg et al., *Structure,* vol. 2, pp. 293–308, 453 (1994).
H. J. Duggleby et al., *Nature,* vol. 373, pp. 264–268 (1995).
*Molecular Cloning –A Laboratory Manual,* Cold Spring Harbor Laboratory Press, N.Y.Y. (1989), vol. 1, 2, and 3 (title pages and tables of contents only).
*Current Protocols in Molecular Biology,* F. M. Ausubel et al., editors, Greene Publishing Associates and Wiley–Interscience, N.Y. (1989) (title pages and table of contents only).

*Primary Examiner*—Robert A. Wax
*Assistant Examiner*—Elizabeth Slobodyansky
*Attorney, Agent, or Firm*—Cheryl J. Tubach; Harry J. Gwinnell

[57] ABSTRACT

The present invention is directed toward efficient, high-yield processes for making ascorbic acid, 2-keto-L-gulonic acid, and esters of 2-keto-L-gulonic acid. The processes comprise reacting the appropriate starting materials with a hydrolase enzyme catalyst such as a protease, an esterase, a lipase or an amidase.

21 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 379 amino acids
( B ) TYPE: Amino Acid
( D ) TOPOLOGY: Linear ( i i ) MOLECULE TYPE: protein ( x i ) SEQUENCE DESCRIPTION: SEQ ID NO:1:

```
Met Met Arg Lys Lys Ser Phe Trp Leu Gly Met Leu Thr Ala Phe Met
 1               5                  10                  15
Leu Val Phe Thr Met Ala Phe Ser Asp Ser Ala Ser Ala Ala Gln Pro
            20                  25                  30
Ala Lys Asn Val Glu Lys Asp Tyr Ile Val Gly Phe Lys Ser Gly Val
            35                  40                  45
Lys Thr Ala Ser Val Lys Lys Asp Ile Ile Lys Glu Ser Gly Gly Lys
        50                  55                  60
Val Asp Lys Gln Phe Arg Ile Ile Asn Ala Ala Lys Ala Lys Leu Asp
 65                  70                  75                  80
Lys Glu Ala Leu Lys Glu Val Lys Asn Asp Pro Asp Val Ala Tyr Val
                85                  90                  95
Glu Glu Asp His Val Ala His Ala Leu Ala Gln Thr Val Pro Tyr Gly
            100                 105                 110
Ile Pro Leu Ile Lys Ala Asp Lys Val Gln Ala Gln Gly Phe Lys Gly
            115                 120                 125
Ala Asn Val Lys Val Ala Val Leu Asp Thr Gly Ile Gln Ala Ser His
        130                 135                 140
Pro Asp Leu Asn Val Val Gly Gly Ala Ser Phe Val Ala Gly Glu Ala
145                 150                 155                 160
Tyr Asn Thr Asp Gly Asn Gly His Gly Thr His Val Ala Gly Thr Val
                165                 170                 175
Ala Ala Leu Asp Asn Thr Thr Gly Val Leu Gly Val Ala Pro Ser Val
            180                 185                 190
Ser Leu Tyr Ala Val Lys Val Leu Asn Ser Ser Gly Ser Gly Thr Tyr
            195                 200                 205
Ser Gly Ile Val Ser Gly Ile Glu Trp Ala Thr Thr Asn Gly Met Asp
        210                 215                 220
Val Ile Asn Met Ser Leu Gly Gly Pro Ser Gly Ser Thr Ala Met Lys
225                 230                 235                 240
Gln Ala Val Asp Asn Ala Tyr Ala Arg Gly Val Val Val Ala Ala
                245                 250                 255
Ala Gly Asn Ser Gly Ser Ser Gly Asn Thr Asn Thr Ile Gly Tyr Pro
            260                 265                 270
Ala Lys Tyr Asp Ser Val Ile Ala Val Gly Ala Val Asp Ser Asn Ser
        275                 280                 285
Asn Arg Ala Ser Phe Ser Ser Val Gly Ala Glu Leu Glu Val Met Ala
    290                 295                 300
Pro Gly Ala Gly Val Tyr Ser Thr Tyr Pro Thr Ser Thr Tyr Ala Thr
305                 310                 315                 320
Leu Asn Gly Thr Ser Met Ala Ser Pro His Val Ala Gly Ala Ala Ala
```

|                      |                      | 325                  |                      |                      |                      | 330                  |                      |                      |                      | 335                  |                      |                      |
|---|---|---|---|---|---|---|---|---|---|---|---|---|

Leu Ile Leu Ser Lys His Pro Asn Leu Ser Ala Ser Gln Val Arg Asn
          340                   345                   350

Arg Leu Ser Ser Thr Ala Thr Tyr Leu Gly Ser Ser Phe Tyr Tyr Gly
          355                   360                   365

Lys Gly Leu Ile Asn Val Glu Ala Ala Ala Gln
          370                   375

(2) INFORMATION FOR SEQ ID NO:2:

(i) SEQUENCE CHARACTERISTICS:
        (A) LENGTH: 584 amino acids
        (B) TYPE: Amino Acid
        (D) TOPOLOGY: Linear (ii) MOLECULE TYPE: protein (xi) SEQUENCE DESCRIPTION: SEQ ID NO:2:

Met Trp Leu Leu Pro Leu Val Leu Thr Ser Leu Ala Ser Ser Ala Thr
 1               5                  10                  15

Trp Ala Gly Gln Pro Ala Ser Pro Val Val Asp Thr Ala Gln Gly
              20                  25                  30

Arg Val Leu Gly Lys Tyr Val Ser Leu Glu Gly Leu Ala Phe Thr Gln
          35                  40                  45

Pro Val Ala Val Phe Leu Gly Val Pro Phe Ala Lys Pro Pro Leu Gly
      50                  55                  60

Ser Leu Arg Phe Ala Pro Pro Gln Pro Ala Glu Pro Trp Ser Phe Val
 65                  70                  75                  80

Lys Asn Thr Thr Ser Tyr Pro Pro Met Cys Cys Gln Asp Pro Val Val
              85                  90                  95

Glu Gln Met Thr Ser Asp Leu Phe Thr Asn Phe Thr Gly Lys Glu Arg
              100                 105                 110

Leu Thr Leu Glu Phe Ser Glu Asp Cys Leu Tyr Leu Asn Ile Tyr Thr
          115                 120                 125

Pro Ala Asp Leu Thr Lys Arg Gly Arg Leu Pro Val Met Val Trp Ile
      130                 135                 140

His Gly Gly Gly Leu Val Leu Gly Gly Ala Pro Met Tyr Asp Gly Val
145                 150                 155                 160

Val Leu Ala Ala His Glu Asn Phe Thr Val Val Val Ala Ile Gln
              165                 170                 175

Tyr Arg Leu Gly Ile Trp Gly Phe Phe Ser Thr Gly Asp Glu His Ser
              180                 185                 190

Arg Gly Asn Trp Gly His Leu Asp Gln Val Ala Ala Leu His Trp Val
          195                 200                 205

Gln Glu Asn Ile Ala Asn Phe Gly Gly Asp Pro Gly Ser Val Thr Ile
          210                 215                 220

Phe Gly Glu Ser Phe Thr Ala Gly Gly Glu Ser Val Ser Val Leu Val
225                 230                 235                 240

Leu Ser Pro Leu Ala Lys Asn Leu Phe His Arg Ala Ile Ser Glu Ser
              245                 250                 255

Gly Val Ala Leu Thr Val Ala Leu Val Arg Lys Asp Met Lys Ala Ala
              260                 265                 270

Ala Lys Gln Ile Ala Val Leu Ala Gly Cys Lys Thr Thr Ser Ala
          275                 280                 285

Val Phe Thr Phe Val His Cys Leu Arg Gln Lys Ser Glu Asp Glu Leu
      290                 295                 300

| Leu<br>305 | Asp | Leu | Thr | Leu | Lys<br>310 | Met | Lys | Phe | Leu | Thr<br>315 | Leu | Asp | Phe | His | Gly<br>320 |
|---|---|---|---|---|---|---|---|---|---|---|---|---|---|---|---|
| Asp | Gln | Arg | Glu | Ser<br>325 | His | Pro | Phe | Leu | Pro<br>330 | Thr | Val | Val | Asp | Gly<br>335 | Val |
| Leu | Leu | Pro | Lys<br>340 | Met | Pro | Glu | Glu | Ile<br>345 | Leu | Ala | Glu | Lys | Asp<br>350 | Phe | Thr |
| Phe | Asn | Thr<br>355 | Val | Pro | Tyr | Ile | Val<br>360 | Gly | Ile | Asn | Lys | Gln<br>365 | Glu | Phe | Gly |
| Trp | Leu<br>370 | Leu | Pro | Thr | Met | Met<br>375 | Gly | Phe | Pro | Leu | Ser<br>380 | Glu | Gly | Lys | Leu |
| Asp<br>385 | Gln | Lys | Thr | Ala | Thr<br>390 | Ser | Leu | Leu | Trp | Lys<br>395 | Ser | Tyr | Pro | Ile | Ala<br>400 |
| Asn | Ile | Pro | Glu | Glu<br>405 | Leu | Thr | Pro | Val | Ala<br>410 | Thr | Phe | Thr | Asp | Lys<br>415 | Tyr |
| Leu | Gly | Gly | Thr<br>420 | Asp | Asp | Pro | Val | Lys<br>425 | Lys | Lys | Asp | Leu | Phe<br>430 | Leu | Asp |
| Leu | Met | Gly<br>435 | Asp | Val | Val | Phe | Gly<br>440 | Val | Pro | Ser | Val | Thr<br>445 | Val | Ala | Arg |
| Gln | His<br>450 | Arg | Asp | Ala | Gly | Ala<br>455 | Pro | Thr | Tyr | Met | Tyr<br>460 | Glu | Phe | Gln | Tyr |
| Arg<br>465 | Pro | Ser | Phe | Ser | Ser<br>470 | Asp | Lys | Phe | Thr | Lys<br>475 | Pro | Lys | Thr | Val | Ile<br>480 |
| Gly | Asp | His | Gly | Asp<br>485 | Glu | Ile | Phe | Ser | Val<br>490 | Phe | Gly | Phe | Pro | Leu<br>495 | Leu |
| Lys | Gly | Asp | Ala<br>500 | Pro | Glu | Glu | Glu | Val<br>505 | Ser | Leu | Ser | Lys | Thr<br>510 | Val | Met |
| Lys | Phe | Trp<br>515 | Ala | Asn | Phe | Ala | Arg<br>520 | Ser | Gly | Asn | Pro | Asn<br>525 | Gly | Glu | Gly |
| Leu | Pro<br>530 | His | Trp | Pro | Phe | Thr<br>535 | Met | Tyr | Asp | Gln | Glu<br>540 | Glu | Gly | Tyr | Leu |
| Gln<br>545 | Ile | Gly | Val | Asn | Thr<br>550 | Gln | Ala | Ala | Lys | Arg<br>555 | Leu | Lys | Gly | Glu | Glu<br>560 |
| Val | Ala | Phe | Trp | Asn<br>565 | Asp | Leu | Leu | Ser | Lys<br>570 | Glu | Ala | Ala | Lys | Lys<br>575 | Pro |
| Pro | Lys | Ile | Lys<br>580 | His | Ala | Glu | Leu | | | | | | | | |

( 2 ) INFORMATION FOR SEQ ID NO:3:

( i ) SEQUENCE CHARACTERISTICS:
        ( A ) LENGTH: 342 amino acids
        ( B ) TYPE: Amino Acid
        ( D ) TOPOLOGY: Linear ( i i ) MOLECULE TYPE: protein ( x i ) SEQUENCE DESCRIPTION: SEQ ID NO:3:

| Met<br>1 | Lys | Leu | Leu | Ser<br>5 | Leu | Thr | Gly | Val | Ala<br>10 | Gly | Val | Leu | Ala | Thr<br>15 | Cys |
|---|---|---|---|---|---|---|---|---|---|---|---|---|---|---|---|
| Val | Ala | Ala | Thr<br>20 | Pro | Leu | Val | Lys | Arg<br>25 | Leu | Pro | Ser | Gly | Ser<br>30 | Asp | Pro |
| Ala | Phe | Ser<br>35 | Gln | Pro | Lys | Ser | Val<br>40 | Leu | Asp | Ala | Gly | Leu<br>45 | Thr | Cys | Gln |
| Gly | Ala<br>50 | Ser | Pro | Ser | Ser | Val<br>55 | Ser | Lys | Pro | Ile | Leu<br>60 | Leu | Val | Pro | Gly |
| Thr<br>65 | Gly | Thr | Thr | Gly | Pro<br>70 | Gln | Ser | Phe | Asp | Ser<br>75 | Asn | Trp | Ile | Pro | Leu<br>80 |

```
Ser  Thr  Gln  Leu  Gly  Tyr  Thr  Pro  Cys  Trp  Ile  Ser  Pro  Pro  Pro  Phe
                    85                      90                       95

Met  Leu  Asn  Asp  Thr  Gln  Val  Asn  Thr  Glu  Tyr  Met  Val  Asn  Ala  Ile
               100                 105                         110

Thr  Ala  Leu  Tyr  Ala  Gly  Ser  Gly  Asn  Asn  Lys  Leu  Pro  Val  Leu  Thr
          115                      120                       125

Trp  Ser  Gln  Gly  Gly  Leu  Val  Ala  Gln  Trp  Gly  Leu  Thr  Phe  Phe  Pro
     130                      135                      140

Ser  Ile  Arg  Ser  Lys  Val  Asp  Arg  Leu  Met  Ala  Phe  Ala  Pro  Asp  Tyr
145                      150                     155                      160

Lys  Gly  Thr  Val  Leu  Ala  Gly  Pro  Leu  Asp  Ala  Leu  Ala  Val  Ser  Ala
                    165                      170                      175

Pro  Ser  Val  Trp  Gln  Gln  Thr  Thr  Gly  Ser  Ala  Leu  Thr  Thr  Ala  Leu
               180                      185                      190

Arg  Asn  Ala  Gly  Gly  Leu  Thr  Gln  Ile  Val  Pro  Thr  Thr  Asn  Leu  Tyr
          195                      200                      205

Ser  Ala  Thr  Asp  Glu  Ile  Val  Gln  Pro  Gln  Val  Ser  Asn  Ser  Pro  Leu
210                      215                           220

Asp  Ser  Ser  Tyr  Leu  Phe  Asn  Gly  Lys  Asn  Val  Gln  Ala  Gln  Ala  Val
225                      230                 235                           240

Cys  Gly  Pro  Leu  Phe  Val  Ile  Asp  His  Ala  Gly  Ser  Leu  Thr  Ser  Gln
                    245                      250                      255

Phe  Ser  Tyr  Val  Val  Gly  Arg  Ser  Ala  Leu  Arg  Ser  Thr  Thr  Gly  Gln
               260                      265                      270

Ala  Arg  Ser  Ala  Asp  Tyr  Gly  Ile  Thr  Asp  Cys  Asn  Pro  Leu  Pro  Ala
          275                      280                      285

Asn  Asp  Leu  Thr  Pro  Glu  Gln  Lys  Val  Ala  Ala  Ala  Ala  Leu  Leu  Ala
     290                      295                      300

Pro  Ala  Ala  Ala  Ala  Ile  Val  Ala  Gly  Pro  Lys  Gln  Asn  Cys  Glu  Pro
305                      310                      315                      320

Asp  Leu  Met  Pro  Tyr  Ala  Arg  Pro  Phe  Ala  Val  Gly  Lys  Arg  Thr  Cys
                    325                      330                      335

Ser  Gly  Ile  Val  Thr  Pro
               340
```

ENZYMATIC PROCESS FOR THE MANUFACTURE OF ASCORBIC ACID 2-KETO-L-GULONIC ACID AND ESTERS OF 2-KETO-L-GULONIC ACID

CROSS REFERENCE TO RELATED APPLICATIONS

This application claims the benefit of U.S. Provisional Application No. 60/017,879, filed on May 17, 1996.

FIELD OF THE INVENTION

This invention relates to processes for the manufacture of ascorbic acid, 2-keto-L-gulonic acid (KLG), and esters of KLG. More particularly, the present invention relates to the use of enzyme catalysts in the manufacture of ascorbic acid, KLG or esters of KLG.

BACKGROUND OF THE INVENTION

Ascorbic acid, also known as vitamin C, is a dietary factor which must be present in the human diet to prevent scurvy and which has been identified as an agent that increases resistance to infection. Ascorbic acid is used commercially, for example, as a nutrition supplement, color fixing agent, flavoring and preservative in meats and other foods, oxidant in bread doughs, abscission of citrus fruit in harvesting and reducing agent in analytical chemistry.

One current method for the manufacture of ascorbic acid utilizes a modification of the original Reichstein-Grossner synthesis (Reichstein et al., *Helv. Chim. Acta,* 17:311 (1934); U.S. Pat. No. 2,301,811 to Reichstein; all references cited herein are specifically incorporated by reference). In this process a glucose source is converted to ascorbic acid. During conversion an intermediate of a diacetonide of KLG is produced.

Several two stage methods exists for the manufacture of ascorbic acid. In the first stage, glucose is converted via fermentation processes to either an isolated intermediate of KLG (Sonoyama et al., *Applied and Envtl. Microbiology,* 43:1064–1069 (1982); Anderson et al., *Science,* 230:144–149 (1985); Shinjoh et al., *Applied and Envtl. Microbiology,* 61:413–420 (1995)) or the intermediate of the Reichstein-Grossner synthesis, the diacetonide of KLG.

The second stage, which converts either of the intermediates to ascorbic acid, proceeds by one of two reported routes. The first route, a modification of the latter steps of the Reichstein-Grossner synthesis, requires a multitude of steps whereby the intermediate is esterified with methanol under strongly acidic conditions to produce methyl-2-keto-L-gulonate (MeKLG). The MeKLG is then reacted with base to produce a metal ascorbate salt. Finally, the metal ascorbate salt is treated with an acidulant to obtain ascorbic acid. The second route is a one-step method comprising acid-catalyzed cyclization of KLG, as originally disclosed in GB Patent No. 466548 to Reichstein) and later modified by Yamazaki (Yamazaki, *J. Agri. Chem. Soc.* Japan, 28:890–894 (1954), and *Chem. Abs.,* 50:5992d) and again by Yodice (WO 87/00839). The Yodice method is commercially undesirable because it uses large amounts of gaseous hydrogen chloride, requires very expensive process equipment and produces an ascorbic acid product requiring extensive purification.

Lipases, a group of hydrolase enzymes, have been used with some success in the synthesis of esters of organic acids. In particular, lipases have been utilized in the transesterification of alcohols in which the esterifying agent is irreversible, such as when vinyl acetate is used as the esterifying agent (Thiel, *Catalysis Today,* 517–536 (1994)). Gutman et. al., *Tetrahedron Lett.,* 28:3861–3864 (1987), describes a process for preparing simple 5-membered ring lactones from gamma-hydroxy methyl esters using porcine pancreatic lipase as the catalyst. However, Gutman et al., *Tetrahedron Lett.,* 28:5367–5368 (1987), later reported that substituting delta-hydroxy methyl esters for gamma-hydroxy methyl esters and using the same catalyst produced only polymers. In EP 0 515 694 A1 to Sakashita et. al., a synthesis of esters of ascorbic acid, which are acylated on the primary hydroxyl group, comprises reacting ascorbic acid with a variety of fatty acid active esters (i.e., fatty acid vinyl esters) in a polar organic solvent in the presence of a lipase.

Thus, there exists a need in the art for methods of producing (a) ascorbic acid or metal salts thereof from KLG or esters of KLG, (b) KLG from esters of KLG and (c) esters of KLG from KLG, which have high yield and high purity with little or no by-product formation and are conducted under mild conditions. Accordingly, it is to the provision of such that the present invention is primarily directed.

SUMMARY OF THE INVENTION

The present invention discloses an advancement in the chemical and biological arts in which a process for preparing ascorbic acid comprises contacting KLG or an ester of KLG with a hydrolase enzyme catalyst.

In another embodiment of the present invention, a process for producing KLG comprises contacting an ester of KLG in an aqueous solution with a hydrolase enzyme catalyst.

In still another embodiment of the present invention, a process for producing esters of KLG from KLG comprises contacting an alcoholic solution of KLG with a hydrolase enzyme catalyst. The alcoholic solution contains an alcohol corresponding to an alkyl moiety of the ester of KLG to be prepared.

In still another embodiment of the present invention, a process for producing esters of KLG from esters of KLG comprises contacting an alcoholic solution of a first ester of KLG with a hydrolase enzyme catalyst. The alcoholic solution contains an alcohol corresponding to an alkyl moiety of a second ester of KLG which is to be prepared.

DETAILED DESCRIPTION OF THE INVENTION

The present invention is directed to the unexpected discovery that ascorbic acid can be formed from KLG or, more preferably, esters of KLG by inducing ring closure of KLG or esters of KLG using a hydrolase enzyme as a catalyst. The process for producing the ascorbic acid may be performed in the melt or in solution. The process may also be performed in vivo or in vitro. For in vivo processes, the hydrolase enzyme catalyst may be naturally occurring within a host cell or may be introduced into a host cell or organism by recombinant DNA methods.

The present invention is also directed to the unexpected discovery that KLG can be prepared in a reversible reaction by reacting an ester of KLG in an aqueous solution using a hydrolase enzyme as a catalyst. Moreover, the present invention is directed to the unexpected discovery that an ester of KLG can be prepared by reacting KLG or another ester of KLG in an alcoholic solution using a hydrolase enzyme as a catalyst. The alcohol used to prepare the solution corresponds to the alkyl moiety of the ester of KLG being prepared.

The hydrolase enzymes for use as catalysts in the processes of the present invention may be derived from or isolated from any appropriate source organisms. Examples of which include, but are not limited to, plants, microorganisms, and animals, such as yeast, bacteria, mold, fungus, birds, reptiles, fish, and mammals. Hydrolase enzymes for the purposes of this invention are defined generally by the enzyme class E.C.3.-.-.-, as defined in *Enzyme Nomenclature* (Academic Press, 1992), and are commercially available.

Preferred hydrolase enzymes are those capable of effecting hydrolysis of molecules containing carbonyl or phosphate groups. More specifically, the preferred hydrolases are capable of effecting hydrolysis at a carbonyl carbon bearing a heteroatom single bond. Examples of such carbonyl carbons bearing a heteroatom single bond include, but are not limited to, esters, thioesters, amides, acids, acid halides, and the like. The preferred hydrolases include the enzyme class E.C.3.1.-.-, which includes hydrolases acting on ester bonds, such as esterases and lipases; the enzyme class E.C.3.2-.-, which includes glycosidases; the enzyme class E.C.3.4-.-, which includes peptide hydrolases, such as proteases; and the enzyme class E.C.3.5.-.-, which includes amidases acting on bonds other than peptide bonds. Most preferred hydrolases include proteases, amidases, lipases, and esterases.

More preferred hydrolases contain an active site serine residue which is capable of undergoing esterification or transesterification with KLG or esters of KLG. Even more preferred are those hydrolases which contain the catalytic triad of serine, histidine and apartic acid.

Preferred proteases include those derived from bacteria of the genera Bacillus or Aspergillus. Particularly preferred proteases are those obtained from the bacteria *Bacillus licheniformis*. Preferred proteases are those containing at least 70% sequence homology with Subtilisin. Proteases having sequence homology with Subtilisin are used in the detergent industry and, therefore, are readily available. More preferred are proteases having at least 80% sequence homology with Subtilisin, even more preferred are proteases having at least 90% sequence homology with Subtilisin and, in particular, proteases having at least 95% sequence homology to Subtilisin. A highly preferred protease is Subtilisin itself having an amino acid sequence (SEQ ID NO: 1) described by Smith et al., *J. Biol. Chem.*, 243:2184–2191 (1968), and given below:

| | | | |
|---|---|---|---|
| MMRKKSFWLG | MLTAFMLVFT | MAFSDSASAA | QPAKNVEKDY |
| IVGFKSGVKT | ASVKKDIIKE | SGGKVDKQFR | IINAAKAKLD |
| KEALKEVKND | PDVAYVEEDH | VAKALAQTVP | YGIPLIKADK |
| VQAQGFKGAN | VKVAVLDTGI | QASHPDLNVV | GGASFVAGEA |
| YNTDGNGHGT | HVAGTVAALD | NTTGVLGVAP | SVSLYAVKVL |
| NSSGSGTYSG | IVSGIEWATT | NGMDVINMSL | GGPSGSTAMK |
| QAVDNAYARG | VVVVAAAGNS | GSSGNTNTIG | YPAKYDSVIA |
| VGAYDSNSNR | ASFSSVGAEL | EVMAPGAGVY | STYPTSTYAT |
| LNGTSMASPH | VAGAAALILS | KHPNLSASQV | RNRLSSTATY |
| LGSSFYYGKG | LINVEAAAQ. | | |

For the convenience of the reader, Table 1 provides a summary of amino acid shorthand used above and in the remainder of the specification.

TABLE 1

| Amino Acid Symbol | Three-Letter Abbreviation | One-Letter |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Also encompassed by the scope of the present invention are proteases corresponding to one to six site-specific mutants, sequence additions, and sequence deletions of the sequence given above. Even more preferred are proteases corresponding to zero to two site-specific mutants of the Subtilisin sequence given above.

Esterases suitable for the present invention include those obtained from pig liver extract. Preferred esterases are those having at least 70% sequence homology with pig liver esterase having an amino acid sequence (SEQ ID NO: 2) described in Matsushima et al., *FEBS Lett.*, 293:37 (1991), and given below:

| | | | |
|---|---|---|---|
| MWLLPLVLTS | LASSATWAGQ | PASPPVVDTA | QGRVLGKYVS |
| LEGLAFTQPV | AVFLGVPFAK | PPLGSLRFAP | PQPAEPWSFV |
| KNTTSYPPMC | CQDPVVEQMT | SDLFTNFTGK | ERLTLEFSED |
| CLYLNIYTPA | DLTKRGRLPV | MVWIHGGGLV | LGGAPMYDGV |
| VLAAHENFTV | VVVAIQYRLG | IWGFFSTGDE | HSRGNWGHLD |
| QVAALHWVQE | NIANFGGDPG | SVTIFGESFT | AGGESVSVLV |
| LSPLAKNLFH | RAISESGVAL | TVALVRKDMK | AAAKQIAVLA |
| GCKTTTSAVF | TFVHCLRQKS | EDELLDLTLK | MKFLTLDFHG |
| DQRESHPFLP | TVVDGVLLPK | MPEEILAEKD | FTFNTVPYIV |
| GINKQEFGWL | LPTMMGFPLS | EGKLDQKTAT | SLLWKSYPIA |
| NIPEELTPVA | TFTDKYLGGT | DDPVKKKDLF | LDLMGDVVFG |
| VPSVTVARQH | RDAGAPTYMY | EFQYRPSFSS | DKFTKPKTVI |
| GDHGDEIFSV | FGFPLLKGDA | PEEEVSLSKT | VMKFWANFAR |
| SGNPNGEGLP | HEPFTMYDQE | EGYLQIGVNT | QAAKRLKGEE |
| VAFWNDLLSK | EAAKKPPKIK | HAEL. | |

Esterases more preferably have at least 80% sequence homology with the sequence of the pig liver esterase given above, even more preferably at least 90% sequence homology, especially preferred at least 95% sequence homology. Highly preferred is the pig liver esterase having the sequence given above.

Also encompassed by the scope of the present invention are esterases corresponding to one to six site-specific mutants, sequence additions, and sequence deletions of the sequence given above. Even more preferred are esterases corresponding to zero to two site-specific mutants of the pig liver esterase sequence given above.

Preferred lipases include those isolated from pigs and other mammals, microorganisms, and plants. This includes, but is not limited to, lipases obtained from the genera Aspergillus, Mucor, Candida, Pseudomonas, Humicola, Rhizopus, Chromobacterium, Alcaligenes, Geotricum, and Penicillium. Preferred lipases also include extracellular lipases, such as cutinases. More preferred lipases have at least 70% sequence homology with Candida Antartica type B lipase, even more preferred have at least 80% sequence homology, still more preferred have at least 90% sequence homology, and even more preferred have at least 95% sequence homology. A highly preferred lipase is the Candida Antartica type B lipase itself which has an amino acid sequence (SEQ ID NO: 3) described by Uppenberg et al., *Structure,* 2:293, 453 (1994), and given below:

For hydrolases containing serine at their active site, the first step in the reaction of either KLG or esters of KLG is believed to involve formation of a KLG-enzyme ester via acylation by KLG of the active site serine. Intra-molecular ring closure is believed to yield ascorbic acid (or its salts), whereas alcoholysis yields an ester of KLG and hydrolysis yields KLG.

The process of the present invention comprises contacting either KLG or an ester of KLG with a hydrolase enzyme to form ascorbic acid. Preferably, this reaction is performed in the presence of an organic solvent system, an aqueous solvent system or a mixture thereof. The organic solvent is preferably a $C_1$–$C_6$ alcohol. The aqueous solvent system or mixed aqueous and organic solvent systems are more preferable because ascorbic acid, KLG, and esters of KLG are generally more soluble in aqueous solvent systems. For the in vitro production of ascorbic acid from esters of KLG, the mixed aqueous and organic solvent systems or organic solvent systems are preferable to minimize competing hydrolysis reactions which can produce KLG as a byproduct. Aqueous solvent systems are especially preferable when utilizing whole cell systems for the production of ascorbic acid in vivo.

In one aspect of the present invention, the ascorbic acid is produced from KLG or esters of KLG in in vivo, whole cell, and whole organism production systems in the presence of the hydrolase enzyme catalyst. In one embodiment, the

| | | | |
|---|---|---|---|
| MKLLSLTGVA | GVLATCVAAT | PLVKRLPSGS | DPAFSQPKSV |
| LDAGLTCQGA | SPSSVSKPIL | LVPGTGTTGP | QSFDSNWIPL |
| STQLGYTPCW | ISPPPFMLND | TQVNTEYMVN | AITALYAGSG |
| NNKLPVLTWS | QGGLVAQWGL | TFFPSIRSKV | DRLMAFAPDY |
| KGTVLAGPLD | ALAVSAPSVW | QQTTGSALTT | ALRNAGGLTQ |
| IVPTTNLYSA | TDEIVQPQVS | NSPLDSSYLF | NGKNVQAQAV |
| CGPLFVIDHA | GSLTSQFSYV | VGRSALRSTT | GQARSADYGI |
| TDCNPLPAND | LTPEQKVAAA | ALLAPAAAAI | VAGPKQNCEP |
| DLMPYARPFA | VGKRTCSGIV | TP. | |

Also encompassed by the scope of the present invention are lipases corresponding to one to six site-specific mutants, sequence additions, and sequence deletions of the sequence given above. Even more preferred are lipases corresponding to zero to two site-specific mutants of the Candida Antartica type B sequence given above.

Preferred amidases include those isolated from bacteria of the genus Penicillium. A more preferred amidase has at least 80% sequence homology with *Penicillin acylase.* A particularly preferred amidase is *Penicillin acylase,* which is also referred to as *Penicillin amidohydrolase,* E.C. 3.5.1.11 (Duggleby et al., *Nature,* 373:264–268 (1995)).

hydrolase enzyme is naturally produced by the host organism. In another embodiment, the hydrolase enzyme is produced by the host organism through recombinant DNA technology. For example, a gene sequence encoding a hydrolase enzyme is inserted in a host organism wherein the host organism may be a microorganism, plant, or animal which is capable of expressing the hydrolase enzyme. The host organism producing the hydrolase enzyme is cultured, i.e. provided with nutrients and a suitable environment for growth, in the presence of KLG or esters of KLG to produce the ascorbic acid. Preferably, the host organism is *Pantoea*

*citrea*, previously referred to as *Erwinia herbicola* as disclosed in U.S. Pat. No. 5,008,193 to Anderson et al.

Also preferably, the host organism is one that produces KLG in addition to producing the hydrolase enzyme. Representative organisms are from the genera Pantoea or Gluconobacter, such as disclosed in Shinjoh et al.,*Applied and Envtl. Microbiology*, 61:413–420 (1995), and the genus Corynebacterium as disclosed in Sonoyama et al., *Applied and Envtl. Microbiology*, 43:1064–1069 (1982).

As used herein, recombinant DNA technology includes in vitro recombinant DNA techniques, synthetic techniques and in vivo recombinant/genetic recombination and is well known in the art. See, for example, the techniques described in Maniatis et al., *Molecular Cloning A Laboratory Manual*, Cold Spring Harbor Laboratory, N.Y. (1989); Ausubel et al., *Current Protocols in Molecular Biology*, Greene Publishing Assoc. and Wiley Interscience, N.Y. (1989); Anderson et al., *Science*, 230:144–149 (1985); and U.S. Pat. No. 5,441,882 to Estell et. al.

For preparations of KLG from esters of KLG, an aqueous solution of the ester of KLG is reacted with the hydrolase enzyme. A co-solvent may be used in the preparation of KLG and is preferably a $C_1$–$C_6$ alcohol.

For preparations of the esters of KLG from KLG or from other esters of KLG, the starting material is in an alcoholic solution wherein the alcohol corresponds to the alkyl moiety of the ester of KLG to be prepared. The alkyl moiety R of the alcohol ROH from which the preferred ester of KLG is derived may be chosen from branched or straight chain, saturated or unsaturated, alkyl, arylalkyls, aryls, and substituted aryls. Preferred R groups include $C_1$ to $C_6$ straight or branched chain, saturated or unsaturated alkyls. Even more preferred esters of KLG that are derived for alkyl moieties include MeKLG, ethyl-KLG, n-propyl-KLG, isopropyl-KLG, n-butyl-KLG, isobutyl-KLG, t-butyl-KLG, and n-pentyl-KLG. The most preferred esters of KLG produced are MeKLG due to its ease of manufacture and butyl-KLG due to the advantageous use of the butanol water azeotroph in water removal. A co-solvent may be used in the preparation of the esters of KLG and is preferably water, a $C_1$–$C_6$ alcohol or a mixture thereof.

Preferred temperatures for conducting the reactions of the present invention are from about 5° C. to about 120° C. Even more preferred temperatures are from about 25° C. to about 100° C., and especially preferred temperatures are from about 38° C. to about 80° C.

The preferred pH for the process of the present invention is between about 1.5 and about 10, and a more preferred pH is between about 3 and about 10. For the preparation of ascorbic acid salts from esters of KLG, a particularly preferred pH range is between about 6 and about 10. For the preparation of ascorbic acid as the free acid, a preferred pH is that under the pKa of ascorbic acid and, more preferred, is that under about 4.2. For the preparation of KLG from esters of KLG, a particularly preferred pH range is between about 5 and about 10 due to the generally enhanced rates of enzyme assisted hydrolysis in this pH range. Alternatively, a pH of between about 1.5 and about 2.5 is particularly desirable for the generation of KLG in protonated form. Finally, for the preparation of esters of KLG from KLG, a particularly preferred pH range is between about 3 and about 6.

Each hydrolase has a temperature optimum, a pH optimum, and a pH and temperature range associated with activity. Thus, the appropriate pH and temperature range for a given hydrolase is that which allows for activity of the hydrolase and avoids conditions which are denaturing or inactivating to the hydrolase. For conditions which may be denaturing, such as high temperature or the use of denaturing solvents such as methanol or the like, a minimal amount of testing may be required to define those hydrolases which remain active under a given set of conditions.

The following examples are offered by way of illustration and are not intended to limit the scope of the claimed invention.

EXAMPLES

Proton and carbon nuclear magnetic resonance (NMR) spectra were recorded on a Varian Gemini 300 NMR instrument operating at 300 MHZ in proton mode and 75 MHZ in carbon mode. All NMR spectra were referenced to tetramethylsilane (TMS) at 0 parts per million (ppm) and peak frequencies were recorded in ppm unless otherwise specified. HPLC (high-performance liquid chromatography) analysis was carried out using ultraviolet (UV) detection. Mass spectra (MS) were obtained using a Fisons VG Analytical Ltd. Autospec Mass Spectrometer in FD (field desorption) mode.

The KLG used in the experiments was obtained by fermentation according to the method of Lazarus et. al., Anderson et al., *Science*, 230:144–149 (1985), and was purified by concentration and crystallization. KLG may alternatively be prepared by chemical conversion from L-sorbose according to methods well known in the art (see e.g., U.S. Pat. No. 2,301,811 to Reichstein). A standard of methyl-2-keto-L-gulonate was purchased from Aldrich Chemical Company (Rare and Specialty Chemicals Catalog), in addition to being prepared by esterification of KLG by methods similar to the procedure used for the preparation of butyl-KLG, described below.

Enzyme hydrolase samples were obtained from commercial sources, including Sigma Chemical Company, Altus Biologics, Recombinant Biocatalysis, Boehringer Mannheim, Novo Nordisk, Genencor International, Thermogen, and Fluka.

Example 1

This example describes the preparation and purification of butyl 2-keto-L-gulonate.

KLG hydrate (51.62 g) was charged in a 500 ml reaction vessel under argon. The reactor was equipped with a 12" vigreux column attached to a Dean Stark trap. The reactor was then charged with n-butanol (310 g) and p-toluene sulfonic acid (2.3 g). The reaction mixture was brought to reflux (81°–82° C.) under mild vacuum (approximately 150 mm Hg) with stirring. Reflux was maintained for a total of two hours and 40 minutes. Heating was discontinued. The reaction was allowed to cool and remain at room temperature for approximately 3 days. The resulting crystals were filtered through a coarse fritted glass filter and washed with two portions of n-butyl alcohol (139 g followed by 37 g). The resulting solids (24.4 g) were dissolved in hot ethyl acetate (250 ml) and recrystallized by standing overnight at room temperature. The recrystallized butyl-KLG was isolated by filtration and dried under vacuum (1.5 mm Hg) until constant weight (15.97 g) was achieved.

The butyl-KLG thus prepared was found to have a solubility of at least 50 weight percent in water as it was soluble at all concentrations under 50 weight percent in water. The recrystallized butyl-KLG of this example had satisfactory proton and carbon NMR spectra and gave the predicted molecular weight by field desorption mass spectrometry.

$^1$H NMR (DMSO, digital resolution=0.11 Hz, TMS at half height=0.5 Hz): 6.49 (OH, d, J=1.4 Hz), 4.96 (OH, d, J=5.0 Hz), 4.84 (OH, d, J=4.8 Hz), 4.78 (OH, d, J=7.4 Hz), 4.17–4.0 (m, 2H), 3.5–3.2 (m, approximately 5H), 1.64–1.5 (m, 2H), 1.4–1.35 (m, 2H), 0.89 (CH$_3$ t, J=7.3).

$^{13}$C NMR (DMSO, decoupled): 169.4, 96.3, 73.8, 72.8, 69.8, 64.5, 62.8, 30.0, 18.4, 13.5.

FDMS: M=250

Example 2

The following procedure was used to demonstrate enzymes for activity under specific pH and aqueous solvent composition conditions.

Initial enzyme screens were carried out as follows. Enzyme (typically 10 mg), aqueous buffer (typically 860 microliters (ul) or 550 ul), aqueous 0.2M CaCl$_2$ (10 ul), methanol (typically 90 ul or 400 ul), and an aqueous solution of substrate (typically 90 ul of butyl-KLG at a typical concentration of 110,000 ppm) were added to a 2 ml polypropylene centrifuge tube. The resulting solution was vortexed briefly and placed on a shaker bath at 300 rpm at 38° C. (typically for 18 hours or more). After incubation, samples were centrifuged at 14,000 G's (14,000 times gravity) for 20 minutes to remove enzyme, sampled (300 ul), and diluted to one milliliter with distilled water. If not analyzed by HPLC within the day, samples were frozen prior to analysis.

Summarized below in Table 2 is the HPLC data of the products (and remaining substrate) upon reaction of butyl-KLG (BuKLG) with a variety of enzyme hydrolases in water/methanol solution. The data were reported in terms of parts per million of KLG, MeKLG, ascorbic acid (ASA) and butyl-KLG. The reporting of a 0 (zero) indicated that the amount of material present was below the detection threshold of the instrument. Samples labeled as "no enzyme" were controls within a given run. The controls contained substrate but no enzyme and thus represented experimental and HPLC background data.

TABLE 2

Enzyme Screen for
Hydrolysis/Methanolysis of Butyl-KLG
(38° C. for 41 Hours/38% Methanol-
Water/0.1 MES Buffer)

| Enzyme | Measured, pH | KLG | MeKLG | ASA | BuKLG (ppm) |
|---|---|---|---|---|---|
| ESL-001-01 | 5.8 | 1180 | 2352 | 766 | 4603 |
| ESL-001-02 | 5.6 | 704 | 1084 | 302 | 7736 |
| ESL-001-03 | 5.7 | 386 | 527 | 257 | 8931 |
| ESL-001-04 | 5.8 | 550 | 752 | 833 | 6229 |
| ESL-001-05 | 5.9 | 456 | 684 | 469 | 7942 |
| ESL-001-06 | 5.6 | 547 | 661 | 129 | 8896 |
| ESL-001-07 | 5.7 | 311 | 755 | 489 | 6540 |
| No Enzyme | | 108 | 325 | 33 | 10177 |
| No Enzyme (repeat) | | 107 | 303 | 0 | 9459 |
| No Enzyme | | 117 | 327 | 42 | 9878 |
| No Enzyme (repeat) | | 103 | 269 | 2 | 8593 |
| No Enzyme | | 116 | 322 | 0 | 9473 |

Table 2 illustrates that the hydrolases provided by Recombinant Biocatalysis (ESL-001-01 through ESL-001-07) showed appreciable conversion of butyl-KLG to ascorbic acid, MeKLG, and KLG in a 38% methanol-water solution buffered with morpholinoethane sulfonic acid (MES) hemisodium salt at a pH controlled between 5.5 and 6. These hydrolase enzymes are sold commercially by Recombinant Biocatalysis as recombinant esterases and lipases from thermophilic organisms under the tradename CloneZyme™.

Example 3

Table 3 below illustrates that a variety of acylases, esterases, lipases, and proteases showed appreciable conversion of butyl-KLG to ascorbic acid, MeKLG, and KLG in a 38% methanol-water solution buffered at pH 4.8 to 5.8 with MES buffer. The enzymes labeled as ChiroClec™ are crystalline crosslinked enzymes sold commercially by Altus Biologics. ChiroClec™ -CR is a lipase from *Candida rugosa*, ChiroClec™ -BL is a crystalline form of Subtilisin (a protease), and ChiroClec™ -PC is a lipase from *Pseudomonas cepacia*. Candida Antartica B (a lipase), pig liver esterase (a hydrolase), and Bacillus Species protease showed particularly high levels of activity.

TABLE 3

Enzyme Screen for Hydrolysis/Methanolysis of Butyl-KLG
(38° C. for 16 Hours/38% Methanol-Water/0.1M MES Buffer)

| Enzyme | Measured pH | KLG | MeKLG | ASA | BuKLG (ppm) |
|---|---|---|---|---|---|
| Pig Liver Esterase | 5.3 | 446 | 4377 | 294 | 5711 |
| *Pseudomonas cepacia* Lipase | 5.3 | 98 | 295 | 65 | 11355 |
| Porcine Pancreatic Lipase | 5.4 | 81 | 316 | 49 | 10709 |
| Candida Rugosa Lipase | 5.7 | 122 | 197 | 180 | 10689 |
| Alpha-Chymotrypsin | 4.9 | 57 | 152 | 20 | 11174 |
| Penicillin Acylase | 5.6 | 83 | 1307 | 15 | 12007 |
| *Aspergillus niger* Lipase | 5.7 | 302 | 541 | 55 | 12290 |
| no enzyme | 5.1 | 88 | 210 | 5 | 10393 |
| no enzyme | 5.1 | 87 | 199 | 1 | 11553 |
| Candida Antartica 'A' Lipase | 5.4 | 88 | 242 | 37 | 10670 |
| Candida lipolytica Lipase | 5.3 | 91 | 92 | 5 | 11604 |
| Candida antartica 'B' Lipase | 4.8 | 2915 | 6807 | 0 | 0 |
| *Humicola lanuginosa* Lipase | 5 | 63 | 90 | 6 | 10191 |
| Bacillus Species Protease | 4.8 | 2587 | 5386 | 9 | 1251 |
| no enzyme | 5.2 | 94 | 194 | 1 | 11552 |
| ChiroCLEC-CR (Dry) | 5.1 | 113 | 222 | 2 | 10988 |
| ChiroCLEC-BL (Dry) | 5.4 | 194 | 642 | 3 | 5123 |
| ChiroCLEC-PC (*Pseudomonas cepacia*) | 5.7 | 147 | 566 | 1 | 10471 |
| *Rhizoipus Delmar* Lipase | 5.5 | 51 | 99 | 1 | 7392 |
| *Rhizopus Niveus* Lipase | 5.1 | 80 | 252 | 17 | 10453 |
| *Rhizopus Oryzae* Lipase | 5.5 | 58 | 172 | 5 | 10873 |
| *Chromobacterium Viscosum* Lipase | 5.5 | 433 | 187 | 1 | 10843 |
| *Geotricum Candidum* Lipase | 5 | 33 | 407 | 7 | 10000 |
| *Mucor Javanicus* Lipase | 5.5 | 33 | 167 | 97 | 9950 |
| *Aspergillus Oryzae* Protease | 5.8 | 289 | 781 | 96 | 7429 |
| Amano-Lipase PS30 (Pseudomonas) | 5.3 | 56 | 300 | 49 | 9143 |
| Amano-Lipase AK (Pseudomonas) | 5.6 | 74 | 167 | 93 | 11372 |

Example 4

Table 4 below illustrates that a variety of acylases, esterases, lipases, and proteases showed appreciable conversion of butyl-KLG to ascorbic acid, MeKLG, and KLG in a 38% methanol-water solution buffered at pH 5 to 5.8 with MES buffer. Pig liver esterase, Subtilisin Carlsberg (a protease), Bacillus species protease, ChiroClec™ -BL, and Candida Antartica B lipase all show particularly high levels of activity.

TABLE 4

Enzyme Screen for Hydrolysis/Methanolysis of Butyl-KLG
(38° C. for 47.5 Hours/38% Methanol-Water/0.1M MES Buffer)

| Enzyme | Measured pH | KLG | MeKLG | ASA | BuKLG (ppm) |
|---|---|---|---|---|---|
| Pig Liver Esterase | 5.3 | 705 | 2720 | 246 | 1368 |
| *Pseudomonas cepacia* Lipase | 5.5 | 77 | 288 | 46 | 6222 |
| Porcine Pancreatic Lipase | 5.4 | 229 | 613 | 222 | 10899 |
| *Candida rugosa* Lipase | 5.8 | 104 | 205 | 155 | 5417 |
| Alpha-Chymotrypsin | 5.1 | 82 | 248 | 54 | 6092 |
| Penicillin Acylase | 5.8 | 100 | 1607 | 30 | 6192 |
| *Aspergillus niger* Lipase | 5.3 | 214 | 391 | 29 | 6470 |
| *Mucor meihei* Lipase | 5.6 | 54 | 189 | 108 | 7041 |
| ChiroCLEC-CR | 5.5 | 115 | 218 | 99 | 3769 |
| Subtilisin Carlsberg | 5.1 | 3072 | 47 | 0 | 0 |
| *Candida antarctica* A | 5.4 | 166 | 316 | 35 | 5943 |
| *Candida lipolytica* Lipase | 5.7 | 150 | 166 | 0 | 6445 |
| *Candida antartica* B | 5.3 | 2210 | 3520 | 60 | 0 |
| *Humicola lanuginosa* Lipase | 5.2 | 129 | 241 | 42 | 8017 |
| Bacillus Sp Protease | 5.3 | 3722 | 1940 | 29 | 38 |
| ChiroCLEC-BL protease | 5 | 3744 | 1724 | 54 | 634 |
| ChiroCLEC PC lipase | 5.7 | 108 | 196 | 5 | 4148 |
| *Candida Rugosa* esterase | 5.6 | 70 | 309 | 61 | 6734 |
| L-1 (Pseudomonas sp)) | 5.4 | 90 | 336 | 11 | 7066 |
| L-2 (*Candida antartica* B) | 5.5 | 2622 | 3764 | 14 | 913 |
| L-3 (*Candida cylindracea*) | 5.7 | 88 | 158 | 37 | 10343 |
| L-5 (*Candida antartica* A) | 5.5 | 153 | 665 | 42 | 4626 |
| L-6 (Pseudomonas sp) | 5.7 | 0 | 379 | 13 | 6183 |
| L-7 (Porcine pancreas) | 5.8 | 94 | 884 | 120 | 5488 |
| L-8 (Humicola sp) | 5.5 | 98 | 219 | 7 | 7299 |
| no enzyme | 5.6 | 75 | 234 | 5 | 5508 |
| no enzyme | 5.5 | 68 | 209 | 6 | 4968 |
| no enzyme | 5.6 | 65 | 277 | 16 | 5320 |

Example 5

Table 5 below illustrates that a variety of lipases and proteases showed appreciable conversion of butyl-KLG to ascorbic acid, MeKLG, and KLG in a 38% methanol-water solution buffered at pH 5.7 to 6.1 with MES buffer. On comparison with the other enzymes in this table, Prozyme 6 (a protease from *Aspergillus oryzae*), Protease 2A (from *Aspergillus oryzae*), and GC899 (a commercial detergent protease from Genencor International) showed higher levels of activity.

TABLE 5

Enzyme Screen for Hydrolysis/Methanolysis of Butyl-KLG
(38° C. for 19 Hours/38% Methanol-Water/0.1 M MES Buffer)

| Enzyme | Comment | Measured pH | KLG | MeKLG | ASA | BuKLG (ppm) |
|---|---|---|---|---|---|---|
| PS30 (Pseudomonas) | Lipase | 5.9 | 83 | 213 | 32 | 10424 |
| GC4 (*Geotricum candidum*) | Lipase | 5.7 | 0 | 166 | 0 | 7475 |
| AK (Pseudomonas) | Lipase | 6 | 27 | 205 | 26 | 9815 |
| G (Penicillium) | Lipase | 5.8 | 0 | 0 | 0 | 9441 |
| Newlase A (Aspergillus) | Protease | 5.9 | 83 | 299 | 6 | 10368 |
| Protease M (Aspergillus) | Protease | 6 | 498 | 1054 | 281 | 6990 |
| Prozyme 6 (Aspergillus) | Protease | 6 | 1489 | 2259 | 0 | 4965 |
| MAP10 (Mucor) | Lipase | 6.1 | 21 | 148 | 145 | 8968 |
| No enzyme | | 5.9 | 71 | 169 | 22 | 9463 |
| No enzyme | | 5.9 | 75 | 191 | 6 | 9391 |
| No enzyme | | 5.9 | 79 | 196 | 7 | 9539 |
| D (Rhizopus) | Lipase | 5.7 | 44 | 156 | 3 | 8562 |
| Newlase II (Rhizopus) | Protease | 5.9 | 36 | 164 | 12 | 9586 |
| AY30 (Candida) | Lipase | 6 | 0 | 192 | 33 | 8725 |
| L-10 (Candida) | Lipase | 5.7 | 0 | 0 | 0 | 9608 |
| CES (Pseudomonas) | Lipase | 5.8 | 52 | 296 | 42 | 9491 |
| N (Rhizopus) | Lipase | 5.8 | 78 | 404 | 27 | 9834 |
| 2A (Protease, Aspergillus) | Protease | 6.1 | 937 | 1158 | 215 | 8951 |
| Hog Pancreatic Lipase | Fluka | 6 | 58 | 529 | 130 | 11114 |
| Lipase (Sigma-1754) | Lipase | 5.8 | 57 | 98 | 47 | 9845 |
| Lipase (Sigma-1754) | Lipase | 5.8 | 46 | 88 | 82 | 9428 |
| Lipase (Sigma-8525) | Lipase | 5.9 | 178 | 222 | 60 | 9041 |
| Lipase (Sigma-1754) | Lipase | 5.7 | 76 | 145 | 89 | 14257 |
| Lipase (Sigma-3126) | Lipase | 5.9 | 90 | 415 | 130 | 12756 |
| F-15 (Rhizopus) | Lipase | 5.8 | 55 | 165 | 14 | 10262 |
| Lipozyme (Novo-Liquid) | Lipase | 6 | 82 | 122 | 160 | 9100 |
| GC899 (protease) | Protease | 5.8 | 791 | 2735 | 312 | 11607 |

Example 6

Table 6 below illustrates that a variety of lipases and proteases showed appreciable conversion of butyl-KLG to ascorbic acid, MeKLG, and KLG in a 8.6% methanol-water solution buffered at a pH of 5.3 to 6 with MES buffer. Protease M (*Aspergillus oryzae*), Prozyme 6 (a protease from *Aspergillus oryzae*), Protease N (Subtilisin), and Protease 2A *Aspergillus oryzae*), all showed particularly high levels of activity.

TABLE 6

Enzyme Screen for Hydrolysis/Methanolysis of Butyl-KLG
(38° for 19 Hours/8.6% Methanol-Water/0.1 M MES)

| Enzyme | Comment | Measured pH | KLG | MeKLG | ASA | BuKLG (ppm) |
| --- | --- | --- | --- | --- | --- | --- |
| PS30 (Pseudomonas) | Lipase | 5.9 | 341 | 163 | 157 | 8363 |
| GC4 (*Geotricum candidum*) | Lipase | 5.9 | 424 | 0 | 8 | 4192 |
| AK (Pseudomonas) | Lipase | 6 | 295 | 432 | 125 | 8255 |
| G (Penicillium) | Lipase | 5.8 | 253 | 323 | 0 | 7678 |
| Newlase A (Aspergillus) | Protease | 5.7 | 692 | 302 | 126 | 13408 |
| R-10 (Penicillium) | Lipase | 6 | 527 | 208 | 583 | 5570 |
| Protease M (Aspergillus) | Protease | 6 | 3650 | 2262 | 328 | 1696 |
| Prozyme 6 (Aspergillus) | Protease | 5.3 | 7207 | 694 | 0 | 0 |
| MAP10 (Mucor) | Lipase | 6 | 369 | 0 | 231 | 8334 |
| No enzyme | | 5.8 | 378 | 239 | 132 | 8272 |
| No enzyme | | 5.8 | 380 | 205 | 19 | 8582 |
| No enzyme | | 5.8 | 382 | 295 | 43 | 8785 |
| D (Rhizopus) | Lipase | 5.9 | 595 | 326 | 76 | 11656 |
| Newlase II (Rhizopus) | Protease | 5.9 | 323 | 212 | 28 | 8535 |
| AY30 (Candida) | Lipase | 5.9 | 330 | 249 | 254 | 10195 |
| L-10 (Candida) | Lipase | 5.8 | 302 | 69 | 55 | 11057 |
| AP12 (Aspergillus) | Lipase | 6 | 1448 | 738 | 129 | 7730 |
| CES (Pseudomonas) | Lipase | 5.9 | 197 | 252 | 0 | 8092 |
| N (Rhizopus) | Lipase | 6 | 582 | 348 | 61 | 9598 |
| N (Protease, Bacillus) | Protease | 5.7 | 1572 | 1289 | 26 | 1822 |
| 2A (Protease, Aspergillus) | Protease | 5.7 | 5891 | 616 | 160 | 764 |
| Hog Pancreatic Lipase | Fluka | 5.8 | 890 | 791 | 158 | 5284 |
| Lipase (Sigma-1754) | Lipase | 5.9 | 283 | 116 | 148 | 6196 |
| Lipase (Sigma-1754) | Lipase | 6 | 348 | 189 | 415 | 8098 |
| Lipase (Sigma-8525) | Lipase | 6 | 326 | 93 | 15 | 4112 |
| Lipase (Sigma-1754) | Lipase | 6 | 300 | 150 | 154 | 8057 |
| Lipase (Sigma-3126) | Lipase | 5.8 | 787 | 488 | 99 | 8829 |
| F-15 (Rhizopus) | Lipase | 5.9 | 218 | 124 | 0 | 8682 |
| Lipozyme (Novo-Liquid) | Lipase | 5.8 | 380 | 95 | 101 | 7251 |
| GC899 (protease) | Protease | 5.6 | 3354 | 1765 | 201 | 6991 |

Example 7

Table 7 below illustrates that a variety of acylases, esterases, lipases, and proteases showed appreciable conversion of butyl-KLG to ascorbic acid, MeKLG, and KLG in a 8.6% methanol-water solution buffered at a pH of approximately 5 to 6 with MES buffer. Candida Antartica B lipase, pig liver esterase, and Bacillus species protease showed particularly high levels of activity.

TABLE 7

Enzyme Screen for Hydrolysis/Methanolysis of Butyl-KLG
(38° C. for 19 Hours/8.6% Methanol-Water/0.1M MES)

| Enzyme | Comment | KLG | MeKLG | ASA | BuKLG |
| --- | --- | --- | --- | --- | --- |
| L-1 (Pseudomonas sp)) | Lipase | 137 | 116 | 47 | 7601 |
| L-2 (*Candida antartica* B) | Lipase | 5249 | 1921 | 0 | 768 |
| L-3 (*Candida cylindracea*) | Lipase | 183 | 64 | 107 | 6920 |
| L-4 (Pseudomonas sp) | Lipase | 239 | 163 | 88 | 9957 |
| L-5 (*Candida antartica* A) | Lipase | 278 | 344 | 0 | 6245 |
| L-6 (Pseudomonas sp) | Lipase | 90 | 219 | 15 | 6613 |
| L-7 (Porcine pancreas) | Lipase | 1007 | 575 | 106 | 5392 |

TABLE 7-continued

Enzyme Screen for Hydrolysis/Methanolysis of Butyl-KLG
(38° C. for 19 Hours/8.6% Methanol-Water/0.1M MES)

| Enzyme | Comment | KLG | MeKLG | ASA | BuKLG |
| --- | --- | --- | --- | --- | --- |
| L-8 (Humicola sp) | Lipase | 209 | 70 | 150 | 7957 |
| no enzyme | | 168 | 152 | 6 | 8753 |
| no enzyme | | 152 | 144 | 3 | 8233 |

TABLE 7-continued

Enzyme Screen for Hydrolysis/Methanolysis of Butyl-KLG
(38° C. for 19 Hours/8.6% Methanol-Water/0.1M MES)

| Enzyme | Comment | KLG | MeKLG | ASA | BuKLG |
| --- | --- | --- | --- | --- | --- |
| no enzyme | | 170 | 137 | 18 | 8157 |
| ESL-001-01 | Recom- | 1271 | 906 | 375 | 4635 |
| ESL-001-02 | binant | 883 | 329 | 332 | 5949 |
| ESL-001-03 | Biocat- | 290 | 123 | 447 | 7333 |
| ESL-001-04 | alysis | 511 | 161 | 306 | 6207 |
| ESL-001-05 | Enzymes | 364 | 124 | 299 | 6402 |
| ESL-001-06 | | 329 | 117 | 118 | 6934 |
| ESL-001-07 | | 0 | 122 | 430 | 15752 |
| Pig Liver Esterase | | 2726 | 3731 | 423 | 10 |
| *Pseudomonas cepacia* Lipase | | 241 | 109 | 224 | 9135 |
| Porcine Pancreatic Lipase | | 333 | 291 | 314 | 7888 |
| *Candida rugosa* Lipase | | 296 | 86 | 451 | 8697 |
| no enzyme | | 153 | 116 | 8 | 8234 |
| Alpha-Chymotrypsin | protease | 330 | 1076 | 65 | 3855 |
| Penicillin Acylase | | 187 | 1248 | 157 | 8110 |
| no enzyme | | 100 | 73 | 3 | 5296 |
| no enzyme | | 144 | 113 | 7 | 8106 |
| *Aspergillus niger* Lipase | | 479 | 72 | 84 | 8455 |

TABLE 7-continued

Enzyme Screen for Hydrolysis/Methanolysis of Butyl-KLG
(38° C. for 19 Hours/8.6% Methanol-Water/0.1M MES)

| Enzyme | Comment | KLG | MeKLG | ASA | BuKLG |
|---|---|---|---|---|---|
| *Mucor meihei* Lipase | | 229 | 278 | 156 | 8620 |
| ChiroCLEC-CR | lipase | 233 | 155 | 11 | 7569 |
| Subtilisin Carlsberg | | 4463 | 93 | 0 | 4428 |
| *Candida antarctica* A | lipase | 215 | 0 | 175 | 7573 |
| *Candida lipolytica* Lipase | | 198 | 62 | 92 | 8445 |
| Bacillus Sp Protease | | 4920 | 642 | 13 | 72 |
| ChiroCLEC-BL protease | | 2860 | 1233 | 135 | 4051 |
| ChiroCLEC PC lipase | | 127 | 62 | 2 | 5653 |
| *Candida Rugosa* esterase | | 178 | 120 | 225 | 9382 |

Example 8

Table 8 below illustrates that a variety of acylases, esterases, lipases, and proteases showed appreciable conversion of butyl-KLG to ascorbic acid, MeKLG, and KLG in a 8.6% methanol-water solution buffered at a pH of approximately 5.8 to 6.2 with MES buffer. Pig liver esterase, Candida Antartica B lipase, Bacillus species protease, and lightly crosslinked crystalline Subtilisin (ChirClec-BL) showed particularly high levels of activity.

TABLE 8

Enzyme Screen for Hydrolysis/Methanolysis of Butyl-KLG
(38° C. for 21 Hours/8.6% Methanol-Water/0.2 M MES

| Enzyme | Comment | pH | KLG | MeKLG | ASA | BUKLG (ppm) |
|---|---|---|---|---|---|---|
| Pig Liver Esterase | | 5.8 | 2373 | 4167 | 717 | 83 |
| *Pseudomonas cepacia* Lipase | | 5.9 | 173 | 169 | 25 | 7384 |
| Porcine Pancreatic Lipase | | 5.9 | 303 | 320 | 78 | 6860 |
| *Candida rugosa* Lipase | | 5.9 | 260 | 112 | 271 | 7351 |
| Alpha-Chymotrypsin | protease | 5.9 | 506 | 1239 | 146 | 4707 |
| Penicillin Acylase | | 6 | 176 | 1172 | 98 | 5392 |
| *Aspergillus niger* Lipase | | 5.9 | 493 | 259 | 84 | 6364 |
| *Mucor meihei* Lipase | | 5.9 | 243 | 283 | 54 | 7067 |
| no enzyme | | 5.9 | 198 | 173 | 2 | 7137 |
| no enzyme | | 5.9 | 216 | 153 | 0 | 7115 |
| no enzyme | | 5.9 | 223 | 154 | 1 | 7319 |
| *Candida Antartica* 'A' Lipase | | 5.9 | 222 | 142 | 148 | 6683 |
| *Candida lipolytica* Lipase | | 6 | 721 | 123 | 25 | 6721 |
| *Candida antartica* 'B' Lipase | | 5.9 | 2708 | 709 | 20 | 28 |
| *Humicola lanuginosa* Lipase | | 5.9 | 176 | 129 | 10 | 7215 |
| Bacillus Species Protease | | 5.8 | 5553 | 603 | 0 | 33 |
| ChiroCLEC-CR (Dry) | | 6.1 | 229 | 170 | 2 | 7191 |
| ChiroCLEC-BL (Dry) | | 5.9 | 4293 | 1282 | 6 | 1376 |
| ChiroCLEC-PC (*P. cepacia*-Dry) | | 6.1 | 240 | 268 | 2 | 7539 |
| *Rhizoipus Delmar* Lipase | | 6 | 178 | 0 | 0 | 7097 |
| *Rhizopus Niveus* Lipase | | 6.2 | 178 | 181 | 61 | 7102 |
| *Rhizopus Oryzae* Lipase | | 6.1 | 159 | 119 | 26 | 7611 |
| *Chromobacterium Viscosum* Lipase | | 6 | 415 | 181 | 2 | 7275 |
| *Geotricum Candidum* Lipase | | 6.1 | 146 | 122 | 6 | 6140 |
| *Mucor Javanicus* Lipase | | 6.2 | 167 | 95 | 141 | 7422 |
| *Aspergillus Oryzae* Protease | | 6.1 | 2193 | 1462 | 39 | 2904 |
| *Candida Rugosa* Esterase | | 5.8 | 129 | 132 | 17 | 7164 |

Example 9

Table 9 below demonstrates the statistical reproduction of the activity detected for highly active enzymes in the preceding examples. Eight of the enzymes from the previous examples, which were identified as showing particularly high levels of activity, were compared under tight pH control. All of the previously identified enzymes with high levels of activity maintained this high level of activity on reanalysis. The enzymes exhibited appreciable conversion of butyl-KLG to ascorbic acid, MeKLG, and KLG in a 8.6% methanol-water solution buffered at a pH of approximately 5.6 to 6 with 0.2M MES buffer. Candida Antartica B lipase, pig liver esterase, and Bacillus species protease showed particularly high levels of activity within this comparative example. Pig liver esterase showed a selectivity toward transesterification as well as significant conversions to ascorbic acid.

TABLE 9

Enzyme Screen for Hydrolysis/Methanolysis of Butyl-KLG
(38° C. for 19 Hours/8.6% Metanol-Water/0.2M MES Buffer)

| Enzyme | Comment | pH | KLG | MeKLG | ASA | BuKLG (ppm) |
|---|---|---|---|---|---|---|
| N Protease | Protease | 6 | 700 | 1166 | 297 | 5435 |
| *Candida Antartica* B | Lipase | 5.8 | 4347 | 2207 | 283 | 0 |
| Pig Liver Esterase | Esterase | 5.9 | 1947 | 4258 | 650 | 0 |
| Bacillus sp Protease | Protease | 5.6 | 5137 | 745 | 55 | 0 |
| ChiroClec-BL (Dry) | Subtilisin | 5.8 | 3485 | 1235 | 215 | 3045 |
| Prozyme-6 | Protease | 5.8 | 3405 | 1518 | 73 | 1624 |
| Protease M | Protease | 6 | 554 | 668 | 271 | 6329 |
| 2A Protease | Protease | 5.9 | 1585 | 1501 | 153 | 3954 |
| no enzyme | | 6 | 135 | 149 | 14 | 8170 |

TABLE 9-continued

Enzyme Screen for Hydrolysis/Methanolysis of Butyl-KLG
(38° C. for 19 Hours/8.6% Metanol-Water/0.2M MES Buffer)

| Enzyme | Comment | pH | KLG | MeKLG | ASA | BuKLG (ppm) |
|---|---|---|---|---|---|---|
| no enzyme | | 5.9 | 136 | 127 | 16 | 8418 |
| no enzyme | | 6 | 142 | 133 | 13 | 8570 |

Example 10

Table 10 below compares the same enzymes as in Example 9 except at a higher concentration of organic solvent. Candida Antartica B and Bacillus species protease showed particularly high levels of activity in that they exhibited appreciable conversion of butyl-KLG to ascorbic acid, MeKLG, and KLG in a 38% methanol-water solution buffered at a pH of approximately 5.6 to 6.2 with 0.2M MES buffer. Decreased, although still appreciable, activity is observed for pig liver esterase relative to that shown in Example 9.

TABLE 10

Enzyme Screen for Hydrolysis/Methanolysis of Butyl-KLG
(38° C. for 19 Hours/38% Methanol-Water/0.2M MES Buffer)

| Enzyme | Comment | pH | KLG | MeKLG | ASA | BuKLG (ppm) |
|---|---|---|---|---|---|---|
| N Protease | Protease | 5.9 | 176 | 1144 | 126 | 8153 |
| Candida Antartica B | Lipase | 5.8 | 1701 | 5710 | 213 | 199 |
| Pig Liver Esterase | Esterase | 6 | 203 | 1654 | 173 | 7030 |
| Bacillus sp Protease | Protease | 5.6 | 3104 | 4032 | 182 | 213 |
| ChiroClec-BL (Dry) | Protease | 5.8 | 1261 | 1693 | 102 | 5572 |
| Prozyme-6 | Protease | 6 | 350 | 1268 | 47 | 7517 |
| Protease M | Protease | 6.2 | 141 | 408 | 199 | 9400 |
| 2A Protease | Protease | 6.1 | 178 | 626 | 90 | 8666 |
| no enzyme | | 6 | 69 | 221 | 8 | 9418 |
| no enzyme | | 5.9 | 61 | 189 | 7 | 8790 |
| no enzyme | | 6 | 63 | 203 | 9 | 9367 |

Example 11

Table 11 below compares the same enzymes as in Example 9 except at a pH buffered around 5.2. Candida Antartica B and pig liver esterase showed particularly high levels of activity in that they exhibited appreciable conversion of butyl-KLG to MeKLG and KLG in a 8.6% methanol-water solution buffered at a pH of approximately 4.9 to 5.3 with 0.2M pyridine/pyridinium hydrochloride buffer. Decreased, although still appreciable, activity is observed for Bacillus species protease relative to Example 9.

TABLE 11

Enzyme Screen for Hydrolysis/Methanolysis of BUKLG
(38° C. for ca. 19 Hours/8.6% Methanol-Water/0.2M Pyridine/
Pyridiniuym Hydrochloride)

| Enzyme | Comment | pH | KLG | MeKLG | ASA | BuKLG (ppm) |
|---|---|---|---|---|---|---|
| N Protease | Protease | 5.2 | 87 | 237 | 47 | 8320 |
| Candida Antartica B | Lipase | 4.9 | 3460 | 3097 | 53 | 0 |
| Pig Liver Esterase | Esterase | 5.2 | 1613 | 5787 | 37 | 390 |
| Bacillus sp Protease | Protease | 5.1 | 1613 | 2473 | 70 | 3757 |

TABLE 11-continued

Enzyme Screen for Hydrolysis/Methanolysis of BUKLG
(38° C. for ca. 19 Hours/8.6% Methanol-Water/0.2M Pyridine/
Pyridiniuym Hydrochloride)

| Enzyme | Comment | pH | KLG | MeKLG | ASA | BuKLG (ppm) |
|---|---|---|---|---|---|---|
| ChiroClec-BL (Dry) | Protease | 5.1 | 987 | 1360 | 67 | 5603 |
| Prozyme-6 | Protease | 5.2 | 700 | 840 | 7 | 6470 |
| Protease M | Protease | 5.3 | 187 | 357 | 0 | 8387 |
| 2A Protease | Protease | 5.2 | 480 | 643 | 0 | 7523 |
| no enzyme | | 5.3 | 97 | 0 | 153 | 9750 |
| no enzyme | | 5.2 | 73 | 0 | 80 | 9547 |

Example 12

Table 12 below compares the same enzymes as in Example 11 except at a higher concentration of organic solvent. Candida Antartica B showed particularly high levels of activity in that it exhibited appreciable conversion of butyl-KLG to MeKLG and KLG in 38% methanol-water solution buffered at a pH of approximately 4.7 to 5.1 with 0.2M pyridine/pyridinium hydrochloride buffer. All of the enzymes showed reduced activity relative to Examples 9 and 11.

TABLE 12

Enzyme Screen for Hydrolysis/Methanolysis of BuKLG
(38° C. for ca. 19 Hours/H 4.9/38% Methanol-Water)

| Enzyme | Comment | pH | KLG | MeKLG | ASA | BuKLG |
|---|---|---|---|---|---|---|
| N Protease | Protease | 4.8 | 0 | 0 | 17 | 9093 |
| Candida Antartica B | Lipase | 4.7 | 1953 | 6470 | 0 | 5373 |
| Pig Liver Esterase | Esterase | 4.9 | 47 | 197 | 0 | 11750 |
| Bacillus sp Protease | Protease | 4.9 | 333 | 2113 | 30 | 10043 |
| ChiroClec-BL (Dry) | Protease | 4.9 | 97 | 447 | 7 | 10950 |
| Prozyme-6 | Protease | 4.9 | 0 | 113 | 3 | 12730 |
| Protease M | Protease | 5.1 | 73 | 203 | 0 | 15887 |
| 2A Protease | Protease | 5 | 67 | 150 | 0 | 13920 |
| no enzyme | | 4.9 | 87 | 13 | 27 | 11753 |

Example 13

Table 13 below compares the same enzymes as in Examples 9 and 11 except at a pH buffered around 2.3. All enzymes tested showed reduced activity relative to Examples 9 and 11 for conversion of butyl-KLG to ascorbic acid, MeKLG, and KLG in a 8.6% methanol-water solution buffered at a pH of approximately 2.3–2.7 with 0.2M phosphate buffer.

TABLE 13

Enzyme Screen for Hydrolysis/Methanolysis of BUKLG
(38° C. for 20 Hours/8.6% Methanol-Water/pH 2.3 0.2M Phosphate Buffer)

| Enzyme | Comment | pH | KLG | MeKLG | ASA | BuKLG |
|---|---|---|---|---|---|---|
| N Protease | Protease | 2.4 | 203 | 0 | 3 | 8980 |
| Candida Antartica B | Lipase | 2.4 | 397 | 323 | 0 | 8463 |
| Pig Liver Esterase | Esterase | 2.4 | 417 | 93 | 0 | 9500 |
| Bacillus Sp Protease | Protease | 2.3 | 347 | 0 | 0 | 10987 |
| ChiroClec-BL (Dry) | Protease | 2.3 | 387 | 0 | 0 | 10580 |
| Prozyme-6 | Protease | 2.4 | 440 | 0 | 0 | 12357 |

TABLE 13-continued

Enzyme Screen for Hydrolysis/Methanolysis of BUKLG
(38° C. for 20 Hours/8.6% Methanol-Water/pH 2.3 0.2M Phosphate Buffer)

| Enzyme | Comment | pH | KLG | MeKLG | ASA | BuKLG |
|---|---|---|---|---|---|---|
| Protease M | Protease | 2.6 | 137 | 333 | 0 | 12237 |
| 2A Protease | Protease | 2.7 | 163 | 347 | 0 | 10600 |
| No enzyme | | 2.3 | 487 | 0 | 0 | 10417 |
| No enzyme | | 2.3 | 413 | 0 | 0 | 9897 |
| No enzyme | | 2.3 | 407 | 0 | 0 | 9873 |

Example 14

Table 14 below compares the first 5 enzymes of Examples 9 and 11 at a buffered pH of about 6 in their ability to catalyze the esterification of KLG to methyl KLG (MeKLG) or their ability to catalyze ring closure of KLG to ascorbic acid. Low levels of activity are observed relative to examples 9 and 11.

TABLE 14

Enzyme Screen for Methanolysis of KLG
(38° C. for 19 Hours/8.6% Methanol-Water/0.2M MES Buffer)

| Enzyme | Comment | pH | KLG | MeKLG | ASA | BuKLG |
|---|---|---|---|---|---|---|
| N Protease | Protease | 6 | 3791 | 0 | 0 | 0 |
| *Candida Antartica* B | Lipase | 6 | 4258 | 0 | 0 | 0 |
| Pig Liver Esterase | Esterase | 6 | 4393 | 0 | 0 | 0 |
| Bacillus sp Protease | Protease | 6 | 4099 | 0 | 0 | 0 |
| ChiroClec-BL (Dry) | Subtilisin | 6.1 | 3270 | 0 | 0 | 0 |
| no enzyme | | 6 | 4340 | 0 | 0 | 0 |
| no enzyme | | 6 | 3295 | 0 | 0 | 0 |
| no enzyme | | 6 | 4029 | 0 | 0 | 0 |

Example 15

Table 15 below demonstrates the production of MeKLG from KLG using Candida Antartica B lipase as catalyst in 8.6% aqueous methanol at a pH of 3–3.2. The buffer was chosen as a mixture of KLG and its sodium salt (approximately 1/9). The first three entries include enzyme catalyst and are the same conditions in triplicate. The second three entries also run in triplicate and are the same conditions as the first three entries except that no enzyme was present. The first three entries show significant esterification of KLG to MeKLG in the presence of Candida Antartica B lipase. The second three entries demonstrate that the conversion does not proceed in the absence of Candida Antartica B lipase.

TABLE 15

Enzyme Screen for Esterification of KLG
68 Hours at 38° C./8.6% Methanol in Aqueous Phase/Buffer = KLG + NaKLG

| Enzyme | Comment | pH | KLG | MeKLG | ASA | BuKLG |
|---|---|---|---|---|---|---|
| *Candida Antartica* B | 8.6% MeOH + KLG | 3.1 | 9227 | 460 | 0 | 0 |
| *Candida Antartica* B | 8.6% MeOH + KLG | 3.1 | 9303 | 530 | 0 | 0 |
| *Candida Antartica* B | 8.6% MeOH + KLG | 3.2 | 9213 | 413 | 0 | 0 |
| no enzyme | 8.6% MeOH + KLG | 2.9 | 9530 | 0 | 0 | 0 |
| no enzyme | 8.6% MeOH + KLG | 2.9 | 9477 | 0 | 0 | 0 |
| no enzyme | 8.6% MeOH + KLG | 2.9 | 9600 | 0 | 0 | 0 |

Example 16

This is example demonstrates the slow decomposition of ascorbic acid under the conditions of HPLC analysis. HPLC sample standards were prepared by dissolving KLG, MeKLG, ascorbic acid (ASA), and butyl-KLG to the appropriate concentration in water. Samples of these standards were placed in filled and sealed vials, stored at room temperature, and analyzed periodically. The HPLC was calibrated on the area response for standards that were injected onto the HPLC as soon as possible after the preparation of the standards. Table 16 below shows the recorded responses for KLG, MeKLG, ascorbic acid, and butyl-KLG standards of 50, 100, and 500 ppm at time 0 (calibration time), at approximately 6.5 hours, approximately 12 hours after sample preparation.

TABLE 16

| Time (minutes) | Amount Prepared | Amount Found KLG | MeKLG | ASA | BuKLG |
|---|---|---|---|---|---|
| 0 | 50 ppm standard | 51 | 51.4 | 53.4 | 50.6 |
| 400 | | 39.9 | 47.7 | 28.3 | 42.7 |
| 715 | | 52 | 43 | 0 | 38.2 |
| 0 | 100 ppm standard | 102 | 103 | 107 | 101 |
| 400 | | 94.3 | 106.8 | 96.6 | 100.1 |
| 715 | | 81.8 | 90.2 | 57.2 | 94.2 |
| 0 | 500 ppm standard | 510 | 514 | 534 | 506 |
| 400 | | 479 | 496 | 487 | 512 |
| 715 | | 493 | 495 | 473 | 499 |

The ascorbic acid responses were non-linear over time with respect to the other standards and, particularly, with respect to standards of 100 ppm or less. Given that the treatment for Examples 2–16 included approximately 16 hours or more at 38° C. on a shaker bath prior to HPLC analysis, it follows that the actual level of ascorbic acid formed was greater than reported.

This invention has been described in detail with particular reference to preferred embodiments thereof, but it will be understood that variations and modifications can be effected within the spirit and scope of the invention.

SEQ ID NO: 1

SEQ ID NO: 2

SEQ ID NO: 3

What is claimed is:

1. A process for preparing ascorbic acid comprising contacting a compound selected from the group consisting of 2-keto-L-gulonic acid and an ester of 2-keto-L-gulonic acid with a hydrolase enzyme catalyst to form ascorbic acid.

2. The process of claim 1 wherein the hydrolase enzyme catalyst is selected from the group consisting of a protease, an esterase, a lipase and an amidase.

3. The process of claim 2 wherein the protease is obtained from a genera selected from the group consisting of Bacillus or Aspergillus.

4. The process of claim 3 wherein the protease is obtained from a *Bacillus licheniformis* bacteria.

5. The process of claim 4 wherein the protease is the Subtilisin protease having the sequence as shown in SEQ ID NO: 1.

6. The process of claim 2 wherein the esterase is obtained from pig liver extract.

7. The process of claim 6 wherein the esterase is the pig liver esterase having the sequence as shown in SEQ ID NO: 2.

8. The process of claim 2 wherein the lipase is obtained from a genera selected from the group consisting of Aspergillus, Mucor, Candida, Pseudomonas, Humicola, Rhizopus, Chromobacterium, Alcaligenes, Geotricum and Penicillium.

9. The process of claim 8 wherein the lipase is the Candida Antartica B lipase having the sequence as shown in SEQ ID NO: 3.

10. The process of claim 2 wherein the amidase is obtained from a genus Penicillium.

11. The process of claim 10 wherein the amidase is the *Penicillin acylase.*

12. The process of claim 1 wherein the hydrolase enzyme catalyst contains an active site serine residue.

13. The process of claim 12 wherein the hydrolase enzyme catalyst contains a catalytic triad of serine, histidine and aspartic acid.

14. The process of claim 1 wherein, prior to contacting the compound with the hydrolase enzyme catalyst, the compound is formed into a solution with a solvent.

15. The process of claim 14 wherein the solvent is selected from the group consisting of water, a $C_1$ to $C_6$ alcohol and a mixture thereof.

16. The process of claim 1 wherein contacting the compound with the hydrolase enzyme catalyst occurs at a pH between about 1.5 and 10.

17. The process of claim 1 wherein contacting the compound with the hydrolase enzyme catalyst occurs at a temperature from about 5° C. to about 120° C.

18. The process of claim 1 wherein, prior to contacting the compound with the hydrolase enzyme catalyst, the hydrolase enzyme catalyst is naturally expressed from a host organism in vivo.

19. The process of claim 1 wherein, prior to contacting the compound with the hydrolase enzyme catalyst, a gene sequence encoding the hydrolase enzyme catalyst is inserted into a host organism and the host organism is cultured to express the hydrolase enzyme catalyst in vivo.

20. The process of claim 19 wherein the host organism is *Pantoea citrea*.

21. The process of claim 18 or claim 19 wherein the host organism produces 2-keto-L-gulonic acid.

* * * * *

UNITED STATES PATENT AND TRADEMARK OFFICE
CERTIFICATE OF CORRECTION

PATENT NO : 5,817,490
DATED : October 6, 1998
INVENTOR(S) : John Clark Hubbs

It is certified that error appears in the above-identified patent and that said Letters Patent is hereby corrected as shown below:

On the second page, after CROSS REFERENCE TO RELATED APPLICATIONS section, column 1, line 11, add:

"GOVERNMENT LICENSE RIGHTS

This invention was made with United States Government support under Cooperative Research Agreement No. 70NANB5H1138 awarded by the Advanced Technology Program of the National Institute of Standards and Technology. The United States Government has certain rights in the invention."

Signed and Sealed this

Fifteenth Day of May, 2001

*Attest:*

NICHOLAS P. GODICI

*Attesting Officer*   *Acting Director of the United States Patent and Trademark Office*